(12) United States Patent
Seidel et al.

(10) Patent No.: US 7,390,624 B2
(45) Date of Patent: Jun. 24, 2008

(54) METAL CHELATE-LABELLED PEPTIDES

(75) Inventors: Christoph Seidel, Weilheim (DE); Ursula-Henrike Wienhues, Krailling (DE); Eva Höss, Starnberg (DE)

(73) Assignee: Roche Diagnostics GmbH, Mannheim (DE)

( * ) Notice: Subject to any disclaimer, the term of this patent is extended or adjusted under 35 U.S.C. 154(b) by 896 days.

(21) Appl. No.: 10/360,647

(22) Filed: Feb. 10, 2003

(65) Prior Publication Data

US 2004/0039178 A1 Feb. 26, 2004

Related U.S. Application Data

(62) Division of application No. 08/776,189, filed as application No. PCT/EP95/02916 on Jul. 24, 1995, now Pat. No. 6,531,572.

(30) Foreign Application Priority Data

Jul. 25, 1994 (DE) .............. P 44 26 276
Aug. 31, 1994 (DE) .............. P 44 30 998

(51) Int. Cl.
*G01N 33/53* (2006.01)
(52) U.S. Cl. ............... 435/7.1; 530/300; 424/208.1
(58) Field of Classification Search .............. 424/188.1, 424/208.1
See application file for complete search history.

(56) References Cited

U.S. PATENT DOCUMENTS

| | | | |
|---|---|---|---|
| 3,780,099 A | 12/1973 | Scanlon et al. | |
| 4,745,076 A | 5/1988 | Müller et al. | |
| 4,849,505 A | 7/1989 | Stavrianopoulos | |
| 4,945,042 A | 7/1990 | Geiger et al. | |
| 5,686,410 A | 11/1997 | Albert et al. | |

FOREIGN PATENT DOCUMENTS

| | | |
|---|---|---|
| DE | 2234905 | 1/1974 |
| EP | 0 580 979 | 10/1985 |
| EP | 0178450 | 4/1988 |
| EP | 0 366 673 | 6/1988 |
| EP | 0 280 211 A2 | 8/1988 |
| EP | 0 307 149 | 9/1988 |
| EP | 0 386 713 | 3/1990 |
| EP | 0 507 587 | 4/1992 |
| EP | 0580979 A2 * | 2/1994 |
| EP | 0 607 103 | 7/1994 |
| JP | 2 155629 | 6/1990 |
| JP | 4 500823 | 2/1992 |
| WO | WO 02734 | 7/1842 |
| WO | 91/01144 | 2/1991 |
| WO | WO 91/0114 | 2/1991 |
| WO | WO 9222571 | 12/1992 |
| WO | WO 86/02734 | 5/1996 |

OTHER PUBLICATIONS

Hornbeck, P., 1991, "Assays for Antibody Production", in Current Protocols in Immunology, John Wiley & Sons, Inc., 2.1.1-2.1.22.*
Devash et al., 1990, *AIDS Res. Hum. Retro.* 6:307-316.
Profy et al., 1990, *J. Immunol.* 144:4641-4647.
Javaherian et al., 1989, *Proc. Natl. Acad. Sci. USA*, 86:6768-6772.
Rajiv Arya and Jean Gariépy, Rapid Synthesis and Introduction of a Protected EDTA- like Group during the Solid-Phase Assembly of Peptides, Bioconjugate Chem., pp. 323-326. vol. 2, No. 5, 1991.
McCafferty, et al., "Synthesis of Redox Derivatives of Lysine and Their Use in Solid-Phase Synthesis of a Light-Harvesting Peptide," *Elsevier Science, Ltd.*, 1995, pp. 1093-1106.
Blackburn, G.F., et al., "Electrochemiluminescence Detection for Development of Immunoassays and DNA Probe Assays for Clinical Diagnostics," *Clinical Chemistry*, 1991, pp. 1-6. vol. 37(9).

\* cited by examiner

*Primary Examiner*—J. S. Parkin
(74) *Attorney, Agent, or Firm*—Rothwell, Figg, Ernst & Manbeck, P.C.

(57) ABSTRACT

The invention concerns a process for the production of metal chelate-labelled peptide antigens, peptides obtainable by this process and their use in an immunological method of detection.

36 Claims, 1 Drawing Sheet

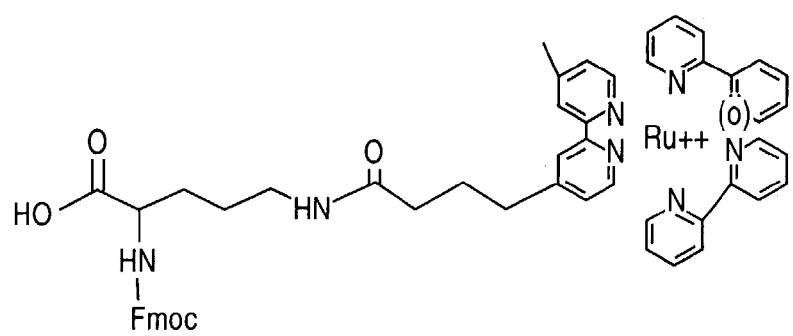

SEQUENCE LISTING

```
<160> NUMBER OF SEQ ID NOS: 29

<210> SEQ ID NO 1
<211> LENGTH: 17
<212> TYPE: PRT
<213> ORGANISM: Artificial Sequence
<220> FEATURE:
<223> OTHER INFORMATION: polypeptide/antigen/epitope

<400> SEQUENCE: 1

Asn Asn Thr Arg Lys Ser Ile Ser Ile Gly Pro Gly Arg Ala Phe Tyr
1               5                   10                  15

Thr

<210> SEQ ID NO 2
<211> LENGTH: 16
<212> TYPE: PRT
<213> ORGANISM: Artificial Sequence
<220> FEATURE:
<223> OTHER INFORMATION: polypeptide/antigen/epitope

<400> SEQUENCE: 2

Asn Asn Thr Arg Ser Ile Ser Ile Gly Pro Gly Arg Ala Phe Tyr Thr
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: polypeptide/antigen/epitope

<400> SEQUENCE: 3

Ile Asp Ile Gln Glu Glu Arg Arg Met Arg Ile Gly Pro Gly Met Ala
1               5                   10                  15

Trp Tyr Ser

<210> SEQ ID NO 4
<211> LENGTH: 24
<212> TYPE: PRT
<213> ORGANISM: Artificial Sequence
<220> FEATURE:
<223> OTHER INFORMATION: polypeptide/antigen/epitope

<400> SEQUENCE: 4

Gln Ala Arg Ile Leu Ala Val Glu Arg Tyr Leu Lys Asp Gln Gln Leu
1               5                   10                  15

Leu Gly Ile Trp Gly Ala Ser Gly
            20

<210> SEQ ID NO 5
<211> LENGTH: 23
<212> TYPE: PRT
<213> ORGANISM: Artificial Sequence
<220> FEATURE:
<223> OTHER INFORMATION: polypeptide/antigen/epitope

<400> SEQUENCE: 5

Leu Gly Ile Trp Gly Cys Ser Gly Lys Leu Ile Cys Thr Thr Ala Val
1               5                   10                  15
```

```
Pro Trp Asn Ala Ser Trp Ser
            20

<210> SEQ ID NO 6
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 6

Lys Asp Gln Gln Leu Leu Gly Ile Trp Gly Ser Ser Gly Lys Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 7

Ala Leu Glu Thr Leu Leu Gln Asn Gln Gln Leu Leu Ser Leu Trp
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 8

Leu Ser Leu Trp Gly Cys Lys Gly Lys Leu Val Cys Tyr Thr Ser
1               5                   10                  15

<210> SEQ ID NO 9
<211> LENGTH: 19
<212> TYPE: PRT
<213> ORGANISM: Artificial Sequence
<220> FEATURE:
<223> OTHER INFORMATION: polypeptide/antigen/epitope

<400> SEQUENCE: 9

Trp Gly Ile Arg Gln Leu Arg Ala Arg Leu Leu Ala Leu Glu Thr Leu
1               5                   10                  15

Leu Gln Asn

<210> SEQ ID NO 10
<211> LENGTH: 27
<212> TYPE: PRT
<213> ORGANISM: Artificial Sequence
<220> FEATURE:
<223> OTHER INFORMATION: polypeptide/antigen/epitope

<400> SEQUENCE: 10

Gln Ala Gln Leu Asn Ser Trp Gly Cys Ala Phe Arg Gln Val Cys His
1               5                   10                  15

Thr Thr Val Pro Trp Pro Asn Asp Ser Leu Thr
            20                  25

<210> SEQ ID NO 11
<211> LENGTH: 15
<212> TYPE: PRT
<213> ORGANISM: Artificial Sequence
```

```
<220> FEATURE:
<223> OTHER INFORMATION: polypeptide/antigen/epitope

<400> SEQUENCE: 11

Ser Arg Arg Phe Ala Gln Ala Leu Pro Val Trp Ala Arg Pro Asp
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: polypeptide/antigen/epitope

<400> SEQUENCE: 12

Pro Gln Asp Val Lys Phe Pro Gly Gly Gly Gln Ile Val Gly Gly Val
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: polypeptide/antigen/epitope

<400> SEQUENCE: 13

Glu Glu Ala Ser Gln His Leu Pro Tyr Ile Glu Gln
1               5                   10

<210> SEQ ID NO 14
<211> LENGTH: 9
<212> TYPE: PRT
<213> ORGANISM: Artificial Sequence
<220> FEATURE:
<223> OTHER INFORMATION: polypeptide/antigen/epitope

<400> SEQUENCE: 14

Gln Lys Ala Leu Gly Leu Leu Gln Thr
1               5

<210> SEQ ID NO 15
<211> LENGTH: 18
<212> TYPE: PRT
<213> ORGANISM: Artificial Sequence
<220> FEATURE:
<223> OTHER INFORMATION: polypeptide/antigen/epitope

<400> SEQUENCE: 15

Ser Arg Gly Asn His Val Ser Pro Thr His Tyr Val Pro Glu Ser Asp
1               5                   10                  15

Ala Ala

<210> SEQ ID NO 16
<211> LENGTH: 28
<212> TYPE: PRT
<213> ORGANISM: Artificial Sequence
<220> FEATURE:
<223> OTHER INFORMATION: polypeptide/antigen/epitope

<400> SEQUENCE: 16

Pro Gln Arg Lys Asn Lys Arg Asn Thr Asn Arg Arg Pro Gln Asp Val
1               5                   10                  15

Lys Phe Pro Gly Gly Gly Gln Ile Val Gly Gly Val
                20                  25
```

```
<210> SEQ ID NO 17
<211> LENGTH: 25
<212> TYPE: PRT
<213> ORGANISM: Artificial Sequence
<220> FEATURE:
<223> OTHER INFORMATION: polypeptide/antigen/epitope

<400> SEQUENCE: 17

Ala Trp Tyr Glu Leu Thr Pro Ala Glu Thr Thr Val Arg Leu Arg Ala
1               5                   10                  15

Tyr Met Asn Thr Pro Gly Leu Pro Val
            20                  25

<210> SEQ ID NO 18
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 18

Asn Thr Thr Arg Ser Ile Ser Ile Gly Pro Gly Arg Ala Phe Tyr
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 19

Ala Val Glu Arg Tyr Leu Lys Asp Gln Gln Leu Leu Gly Ile Trp
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: polypeptide/antigen/epitope

<400> SEQUENCE: 20

Leu Gly Ile Trp Gly Cys Ser Gly Lys Leu Ile Cys Thr Thr Ala Val
1               5                   10                  15

<210> SEQ ID NO 21
<211> LENGTH: 19
<212> TYPE: PRT
<213> ORGANISM: Artificial Sequence
<220> FEATURE:
<223> OTHER INFORMATION: polypeptide/antigen/epitope

<400> SEQUENCE: 21

Gly Cys Ser Gly Lys Leu Ile Cys Thr Thr Ala Val Pro Trp Asn Ala
1               5                   10                  15

Ser Trp Ser

<210> SEQ ID NO 22
<211> LENGTH: 14
<212> TYPE: PRT
<213> ORGANISM: Artificial Sequence
<220> FEATURE:
<223> OTHER INFORMATION: polypeptide/antigen/epitope

<400> SEQUENCE: 22
```

Asn Ser Trp Gly Cys Ala Phe Arg Gln Val Cys His Thr Thr
1               5                   10

<210> SEQ ID NO 23
<211> LENGTH: 9
<212> TYPE: PRT
<213> ORGANISM: Artificial Sequence
<220> FEATURE:
<223> OTHER INFORMATION: polypeptide/antigen/epitope

<400> SEQUENCE: 23

Lys Asn Lys Arg Asn Thr Asn Arg Arg
1               5

<210> SEQ ID NO 24
<211> LENGTH: 25
<212> TYPE: PRT
<213> ORGANISM: Artificial Sequence
<220> FEATURE:
<223> OTHER INFORMATION: polypeptide/antigen/epitope

<400> SEQUENCE: 24

Lys Asn Lys Arg Asn Thr Asn Arg Arg Pro Gln Asp Val Lys Phe Pro
1               5                   10                  15

Gly Gly Gly Gln Ile Val Gly Gly Val
            20                  25

<210> SEQ ID NO 25
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 25

Leu Ala Glu Gln Phe Lys Gln Gln Ala Leu Gly Leu Leu Gln Thr
1               5                   10                  15

<210> SEQ ID NO 26
<211> LENGTH: 30
<212> TYPE: PRT
<213> ORGANISM: Artificial Sequence
<220> FEATURE:
<223> OTHER INFORMATION: polypeptide/antigen/epitope

<400> SEQUENCE: 26

Lys Asn Lys Arg Asn Thr Asn Arg Arg Pro Gln Asp Val Lys Phe Pro
1               5                   10                  15

Gly Gly Gly Gln Ile Val Gly Gly Val Leu Leu Pro Arg Arg
            20                  25                  30

<210> SEQ ID NO 27
<211> LENGTH: 15
<212> TYPE: PRT
<213> ORGANISM: Artificial Sequence
<220> FEATURE:
<223> OTHER INFORMATION: polypeptide/antigen/epitope

<400> SEQUENCE: 27

Asn Pro Lys Pro Gln Lys Lys Asn Lys Arg Asn Thr Asn Arg Arg
1               5                   10                  15

<210> SEQ ID NO 28
<211> LENGTH: 18
<212> TYPE: PRT
<213> ORGANISM: Artificial Sequence

```
<220> FEATURE:
<223> OTHER INFORMATION: polypeptide/antigen/epitope

<400> SEQUENCE: 28

Gly Gln Ile Val Gly Gly Val Tyr Leu Leu Pro Arg Arg Gly Pro Arg
1               5                   10                  15

Leu Gly

<210> SEQ ID NO 29
<211> LENGTH: 9
<212> TYPE: PRT
<213> ORGANISM: Artificial Sequence
<220> FEATURE:
<223> OTHER INFORMATION: polypeptide/antigen/epitope

<400> SEQUENCE: 29

Ser Gln His Leu Pro Tyr Ile Glu Gln
1               5
```

US 7,390,624 B2

METAL CHELATE-LABELLED PEPTIDES

CROSS REFERENCE TO RELATED APPLICATIONS

This application is a divisional application of U.S. application Ser. No. 08/776,189, filed Jan. 24, 1997 now U.S. Pat. No. 6,531,572, which is a national stage filing under 35 U.S.C. § 371 of PCT/EP95/02916, filed Jul. 24, 1995. This application further claims priority under 35 U.S.C. § 119 to foreign applications P 44 26 276.0 (DE), filed Jul. 25, 1994, and P 44 30 998.8 (DE), filed Aug. 31, 1994. The disclosures of all of the above identified applications are hereby incorporated by reference.

DESCRIPTION

The present invention concerns a process for the production of metal chelate-labelled peptides, metal chelate-labelled peptides obtainable by this process and the use of these peptides in an immunological method of detection.

The detection of immunoglobulins in body fluids, in particular in human sera, is used to diagnose infections with microorganisms, in particular viruses, such as HIV, hepatitis viruses etc. The presence of specific immunoglobulins in the examined sample is usually detected by reaction with one or several antigens that react with the specific immunoglobulins. Methods for the determination of specific immunoglobulins in the sample liquid must be sensitive, reliable, simple and rapid.

In recent years more and more detection systems based on non-radioactive marker groups have been developed in which the presence of an analyte, e.g. a specific antibody, in the examined sample can be determined with the aid of optical (e.g. luminescent or fluorescent), NMR-active or metal-precipitating detection systems.

EP-A-0 307 149 discloses an immunological test for an antibody in which two recombinant polypeptides are used as antigens one of which is immobilized on a solid phase and the other carries a marker group and both recombinant antigens are expressed in different organisms to increase the specificity of the test.

EP-A-0 366 673 discloses a method for the detection of antibodies in a sample in which an antibody is detected by reaction with a purified labelled antigen and with the same purified antigen in a solid phase-bound form. Human IgG is for example disclosed as an antigen.

EP-A-0 386 713 describes a method for the detection of antibodies against HIV using two solid supports in which various HIV antigens are immobilized on the two solid supports each of which is brought into contact with an aliquot of a sample and with a labelled HIV antigen wherein the presence of antibodies is detected by a positive reaction in at least one of the tests. Recombinantly produced polypeptides are disclosed as HIV antigens.

EP-A-0 507 586 describes a method for carrying out an immunological test for a specific immunoglobulin in which a sample is brought into contact with two antigens capable of binding the immunoglobulin, wherein the first antigen carries a group suitable for binding to a solid support and the second antigen carries a marker group. The marker group can be a direct marker group e.g. an enzyme, a chromogen, a metal particle, or also an indirect marker group i.e. the marker group attached to the antigen can react with a receptor for the marker group which in turn carries a signal-generating group. A fluorescein derivative is mentioned as an example of such an indirect marker group, the receptor of which is an antibody which in turn is coupled to an enzyme. Polypeptides such as the hepatitis B surface antigen are disclosed as antigens. SH groups are introduced into this antigen by derivatization which are used to couple the fluorescein.

EP-A-0 507 587 discloses a specific method suitable for the detection of IgM antibodies in which the sample is incubated with a labelled antigen which is directed against the antibody to be detected and with a second antibody which is also directed against the antibody to be detected and is capable of binding to a solid phase.

EP-A-0 199 804 and EP-A-0 580 979 disclose an immunological method of detection using antigens which are labelled with luminescent metal chelate groups in particular with ruthenium and osmium chelate groups. Immunoglobulins are used as antigens which are statistically labelled by reaction with activated metal complexes.

EP-A-0 178 450 discloses metal chelates in particular ruthenium complexes to which an immunologically active material, for example antibodies, can be coupled. The coupling is achieved by the statistical reaction of the immunologically reactive material with the metal chelate.

EP-A-0 255 534 discloses a luminescence immunoassay using a metal chelate-coupled antigen or antibody. The coupling is for example achieved by the statistical reaction of a metal chelate active ester derivative with an antibody.

WO 90/05301 discloses a method for the detection and for the quantitative determination of analytes by electrochemiluminescence using luminescent metal chelates which are coupled to (i) an added analyte, (ii) a binding partner of the analyte or (iii) a reactive component which can bind to (i) or (ii). The luminescence is measured after binding the metal chelate to activated and optionally magnetic microparticles.

In the immunological methods for detecting antibodies known from the state of the art polypeptide antigens are usually used which are normally produced by recombinant DNA methods. However, problems may occur when using such polypeptide antigens. Thus recombinant polypeptides can often only be produced in the form of fusion polypeptides in which case the fused part can lead to false positive results in the test. In addition polypeptides produced by recombinant expression often only have a very low stability in the sample solution and tend to aggregate. A further disadvantage is that it is often not possible to selectively and reproducibly introduce marker groups into such polypeptides.

Moreover the production of recombinant polypeptide antigens involves high costs and large variations in the immunological reactivity in different lots of the recombinant polypeptide antigens can occur.

The object of the present invention was therefore to provide a process with which antigens for immunological tests can be produced in a simple and efficient manner wherein the disadvantages of the antigens known from the state of the art are at least partially eliminated. In addition the process should enable a selective and reproducible introduction of marker groups into the antigens.

This object is achieved by a process for the production of metal chelate-labelled peptides which is characterized in that a peptide having the desired amino acid sequence is synthesized on a solid phase in which (a) after the synthesis an activated luminescent metal chelate is coupled to the N-terminal primary amino group of the peptide or/and (b) an amino acid derivative is introduced during the synthesis at at least one position of the peptide which is covalently coupled with a luminescent metal chelate marker group.

The peptides produced by the process according to the invention preferably have a maximum length of 50 amino acids, particularly preferably of 30 amino acids at most and are excellently suitable for immunological methods of detection and in particular for the determination of specific immunoglobulins. Surprisingly it was found that the peptides produced by the process according to the invention have a high affinity and specificity for the immunoglobulins to be detected despite the presence of bulky metal chelate marker groups.

The process according to the invention enables metal chelate marker groups to be introduced selectively with regard to their location as well as with regard to their number. In the peptide synthesis according to the invention it is namely possible by selective incorporation of metal chelate-labelled amino acid derivatives to specifically select those positions on the peptide at which a label will be introduced. In this manner one achieves an improved reproducibility and sensitivity of immunological tests in which peptides produced according to the invention are used.

A further advantage of the process according to the invention is that the use of peptide antigens enables all antibody classes such as IgG, IgM, IgE and IgA to be recognized. Also the test is less susceptible to interference by using defined small and stable antigens which do not tend to aggregate.

The metal chelates that are coupled by the process according to the invention to the peptide are luminescent metal chelates i.e. metal chelates which produce a detectable luminescence reaction. This luminescence reaction can for example be detected by fluorescence or by electrochemiluminescence measurement. The metal of these metal chelates is for example a transition metal or a rare earth metal. The metal is preferably ruthenium, osmium, rhenium, iridium, rhodium, platinum, indium, palladium, molybdenum, technetium. copper, chromium or tungsten. Ruthenium, iridium, rhenium and osmium are especially preferred. Ruthenium is most preferred.

The ligands which form the metal chelate together with the metal are usually polydentate ligands i.e. ligands with several coordination positions. Polydentate ligands comprise for example aromatic and aliphatic ligands. Suitable aromatic polydentate ligands include aromatic heterocyclic ligands. Preferred aromatic heterocyclic ligands are nitrogen-containing polyheterocycles such as for example bipyridyl, bipyrazyl, terpyridyl and phenanthrolyl. These ligands can for example contain substituents such as alkyl, substituted alkyl, aryl, substituted aryl, aralkyl, carboxylate, carboxyaldehyde, carboxamide, cyano, amino, hydroxy, imino, hydroxycarbonyl, aminocarbonyl, amidine, guanidinium, ureide, sulphur-containing groups, groups containing phosphorus and the carboxylate esters of N-hydroxy-succinimide. The chelate can also contain one or several monodentate ligands. Examples of monodentate ligands encompass carbon monoxide, cyanide, isocyanide, halogenide and aliphatic, aromatic and heterocyclic phosphines, amines, stilbenes and arsines.

The luminescent metal chelate is particularly preferably selected from metal chelates with bipyridyl or phenanthrolyl ligands. Examples of suitable metal chelates and the production thereof are described in EP-A-0 178 450, EP-A-0 255 534, EP-A-0 580 979 and WO 90/05301. Reference is hereby made to this disclosure. The most preferred metal chelates are ruthenium-(bipyridyl)$_3$-chelates. These chelates are commercially available in the form of active ester derivatives e.g. from Igen Inc. (Rockville, Md., USA).

According to variant (a) of the process according to the invention the metal chelate label is introduced into the peptide after synthesis of the desired amino acid sequence by selective reaction of the N-terminal primary amino group of the peptide with an activated metal chelate e.g. a metal chelate active ester derivative. The activated metal chelate is preferably coupled before cleaving the peptide from the solid phase and before cleaving the protecting groups on reactive side chains of the amino acid derivatives used for the peptide synthesis.

In variant (b) of the process according to the invention an amino acid derivative is introduced during the solid phase synthesis which is covalently coupled to a luminescent metal chelate marker group. The metal chelate marker group is preferably coupled to an amino group in particular to a primary amino group of the amino acid derivative. If it is indended to introduce the marker group during the synthesis at the amino terminus of the peptide sequence, the metal chelate can be coupled to a free amino group of the N-terminal amino acid. If it is intended to introduce the marker group within the sequence, the metal chelate is preferably coupled to the primary amino side group of an amino acid such as lysine or ornithine. Amino acid-metal chelate derivatives can for example be produced by coupling an activated metal chelate e.g. a metal chelate active ester derivative to a free primary amino group of an optionally partially protected amino acid derivative. A preferred metal chelate-coupled lysine derivative is shown in FIG. 1.

The term "active ester" within the sense of the present invention encompasses activated ester groups that can react with free amino groups of peptides under such conditions that no interfering side reactions with other reactive groups of the peptide can occur. An N-hydroxy-succinimide ester is preferably used as the active ester derivative. In addition to the N-hydroxysuccinimide esters it is also possible to use analogous p-nitro-phenyl, pentafluorophenyl, imidazolyl or N-hydroxybenzo-triazolyl esters.

In the process according to the invention the peptide having the desired amino acid sequence is synthesized on a solid phase-preferably using a commercial peptide synthesizer (e.g. the instruments A 431 or A 433 from Applied Biosystems). The synthesis is carried out according to known methods preferably starting at the carboxyl terminus of the peptide using amino acid derivatives. Amino acid derivatives are preferably used whose amino terminal group required for coupling is derivatized with a fluorenylmethyloxycarbonyl (Fmoc) residue. Reactive side groups of the amino acids used contain protecting groups that can be readily cleaved off after completion of the peptide synthesis. Preferred examples of this are protecting groups such as triphenylmethyl (Trt), t-butyl ether (tBu), t-butyl ester (0 tBu), tert.-butoxycarbonyl (Boc) or 2,2,5,7,8-penta-methylchroman-6-sulfonyl (Pmc).

The amino side chains of lysine residues or of other amino acid derivatives with primary amino side groups that are located at positions of the peptide at which it is intended to introduce a label are covalently coupled with a metal chelate according to variant (b).

In addition to the 20 natural amino acids the peptide can also contain artificial amino acids such as β-alanine, γ-amino-butyric acid, ε-amino-caproic acid, norleucine or ornithine. These artificial amino acids are used for the synthesis in a protected form analogously to the natural amino acids.

According to variant (a) of the process according to the invention the metal chelate label is introduced after completion of the synthesis by reacting the preferably solid phase-bound peptide with the activated metal chelate which is desired in each case which reacts with free primary amino groups of the N-terminal amino acid of the peptide. 1.5 to 4 equivalents active ester are preferably used per free primary amino group. Subsequently if necessary the reaction product is cleaved from the solid phase and the protecting groups are then purified preferably by HPLC.

If the peptide still contains amino groups that are derivatized with a second protecting group such as phenylacetyl then these protecting groups are removed in the last step. Phenylacetyl protecting groups can for example be enzymatically removed at room temperature with immobilized or soluble penicillin G amidase in aqueous solution containing an organic solvent.

If the peptides produced by the process according to the invention contain an intramolecular disulfide bridge, then the peptide sequence can be oxidized on the solid phase with for example iodine in hexafluoroisopropanol/dichloromethane (Kamber and Hiskey in Gross E. and Meienhofer J., The Peptides, Academic Press, New York, 1981, pages 145 to 147) after completion of the synthesis but before cleaving the N-terminal Fmoc-protecting group of the last amino acid, and subsequently the N-terminal Fmoc-protecting group is cleaved.

A peptide is preferably synthesized which contains an immunologically reactive epitope region, i.e. an antibody-binding peptide sequence, and a spacer region. In this case at least one metal chelate label is preferably coupled to the spacer region. Peptides in which the label is located in the spacer region often have a better sensitivity in immunological tests.

The spacer region which preferably has a length of 1 to 10 amino acids has a stabilizing and solubilizing effect since it preferably contains charges or/and can form hydrogen bridges. In addition it can sterically facilitate the binding of several, e.g. high molecular receptors, to the metal chelate-labelled peptide. The amino acids of the spacer region are preferably selected from the group comprising glycine, β-alanine, γ-amino-butyric acid, ε-aminocaproic acid, lysine and compounds having the structural formula $NH_2—[(CH_2)_n O]_x—CH_2—CH_2—COOH$ in which n is 2 or 3 and x is 1 to 10. In addition the spacer region preferably contains at least some artificial amino acid derivatives. The spacer region is preferably located at the amino terminus or/and at the carboxy terminus of the peptide.

Peptides are preferably synthesized by the process according to the invention which contain an epitope region from pathogenic organisms e.g. bacteria, viruses and protozoa or from autoimmune antigens. The immunologically reactive epitope region is preferably derived from viral antigens e.g. the amino acid sequences of HIV I, HIV II, HIV subtype O or hepatitis C virus (HCV).

Preferably HIV I, HIV II and HIV subtype O epitopes are selected from the regions gp32, gp41 and gp120. HCV epitopes are preferably selected from the Core/Env region of the non-structural protein regions NS3, NS4 or NS5, The epitope region of HIV I, HIV II or HIV subtype O amino acid sequences is particularly preferably selected from the group of amino acid sequences:

| | |
|---|---|
| NNTRKSISIG PGRAFYT (SEQ ID NO: 1) | (I) |
| NTTRSISIGP GRAFYTC (SEQ ID NO: 2) | (II) |
| IDIQEERRMR IGPGMAWYS (SEQ ID NO: 3) | (III) |
| QARILAVERY LKDQQLLGIW GASG (SEQ ID NO: 4) | (IV) |
| LGIWGCSGKL ICTTAVPWNA SWS (SEQ ID NO: 5) | (V) |
| KDQQLLGIWG SSGKL (SEQ ID NO: 6) | (VI) |
| ALETLLQNQQ LLSLW (SEQ ID NO: 7) | (VII) |
| LSLWGCKGKL VCYTS (SEQ ID NO: 8) | (VIII) |
| WGIRQLRARL LALETLLQN (SEQ ID NO: 9) and | (IX) |
| QAQLNSWGCA FRQVCHTTVP WPNDSLT (SEQ ID NO: 10) | (X) | or partial sequences thereof which have a length of at least 6 and preferably of at least 8 amino acids.

The amino acid sequences I to III are derived from the gp120 region of HIV I, the amino acid sequences IV to IX are derived from the gp41 region of HIV I and the amino acid sequence X is derived from the gp32 region of HIV II. The amino acid sequences I to X are also shown in the sequence protocols SEQ ID NO. 1 to SEQ ID NO. 10. Each of the sequences V, VIII and X contain two cysteines which are preferably present in the form of a disulfide bridge. These sequences preferably contain an N-terminal or/and a C-terminal spacer as defined above which carries a metal chelate label. Lysine residues located within the epitope region can also optionally be present in a labelled form.

The epitope region of HCV amino acid sequences is preferably selected from the group of amino acid sequences:

| | |
|---|---|
| SRRFAQALPV WARPD (SEQ ID NO: 11) | (XI) |
| PQDVKFPGGG QIVGGV (SEQ ID NO: 12) | (XII) |
| EEASQHLPYI EQ (SEQ ID NO: 13) | (XIII) |
| QKALGLLQT (SEQ ID NO: 14) | (XIV) |
| SRGNHVSPTH YVPESDAA (SEQ ID NO: 15) | (XV) |
| PQRKNKRNTN RRPQDVKFPG GGQIVGGV (SEQ ID NO: 16) | (XVI) |
| and | |
| AWYELPAET TVRLRAYMNT PGLPVA (SEQ ID NO: 17) | (XVII) | or partial sequences thereof which have a length of at least 6 and preferably at least 8 amino acids. The sequence XI is derived from the NS5 region, the sequences XII and XVI from the Core region, the sequences XIII, XIV and XV from the NS4 region and the sequence XVII is derived from the NS3 region of HCV. The amino acid sequences XI to XVII are shown in the sequence protocols SEQ ID NO. 11 to SEQ ID NO. 17. Peptides with the above-mentioned epitopes preferably contain an additional spacer region which carries a metal chelate label.

A further subject matter of the present invention is a metal chelate-labelled peptide which has a maximum length of 50 and preferably of 30 amino acids and whose amino terminus or/and amino side groups are coupled with at least one luminescent metal chelate, preferably a metal chelate-active ester derivative. The luminescent metal chelate is preferably a ruthenium chelate.

The peptide according to the invention preferably contains an immunologically reactive epitope region that can react with antibodies from for example human sera and an immunologically non-reactive spacer region wherein the spacer region carries at least one metal chelate label. The spacer region is preferably located at the amino terminus of the peptide and has a length of 1 to 10 amino acids. The epitope region is preferably derived from the amino acid sequences of HIV I or HCV II including variants e.g. subtypes thereof e.g. HIV subtype O and is one of the amino acid sequences I to XVII or a partial sequence thereof.

The present invention also concerns the use of metal chelate-labelled peptides as antigens in an immunological method for the determination of specific antibodies in a sample liquid. Such antibodies are preferably determined which indicate an infection by microorganisms such as bacteria, viruses or protozoa. Antibodies directed against viruses e.g. antibodies directed against HIV or hepatitis viruses are particularly preferably determined. The sample liquid is preferably serum and particularly preferably human serum. In addition it is preferred that the metal chelate-labelled peptides according to the invention are used in an immunological method in a bridge test format.

The present invention also concerns a method for the immunological determination of a specific antibody in a sample liquid which is characterized in that the sample liquid is incubated with a first labelled antigen which is directed against the antibody to be determined and comprises a metal chelate-labelled peptide as defined above and the antibody is detected by means of a binding to the peptide. A peptide labelled with a ruthenium, rhenium, iridium or osmium chelate is preferably used as the first antigen.

The immunological method of determination according to the invention can in fact be carried out according to any known test format e.g. in a homogeneous immunoassay with a single reaction phase or in a heterogeneous immunoassay with more than one reaction phase. A heterogeneous test format is preferably used in which the presence of the antibody is detected in the presence of a solid phase. One embodiment of this test format is the so-called double antigen bridge test design. In this case the sample liquid is incubated in the presence of a solid phase with the first antigen and with a second antigen which is directed against the antibody to be determined and (a) is bound to the solid phase or (b) is present in a form capable of binding to the solid phase.

The antibody to be determined in the sample liquid is detected by determining the label in the solid phase or/and in the liquid phase. The second antigen is preferably labelled with biotin and is capable of binding to a solid phase which is coated with streptavidin or avidin. A peptide labelled with biotin is preferably used as the second antigen.

The test procedure preferably comprises mixing the sample liquid with the first antigen and the second antigen on the solid phase in order to obtain a labelled immobilized complex of first antigen, antibody and solid phase-bound second antigen. Compared to other test formats for detecting antibodies, the bridge test format leads to an improvement in sensitivity i.e. all immunoglobulin classes such as IgG, IgM, IgA and IgE are recognized as well as in specificity i.e. the unspecific reactivity is reduced.

A further advantage of the double antigen bridge test format in which a solid phase-bound and a metal chelate-labelled peptide are used as antigens is that it is possible to reduce the risk of a false negative evaluation of samples which have a high titre of the antibody to be determined as a result of the Hook effect and namely by increasing the number of marker groups per peptide preferably to 2 to 10 marker groups. The increase in the number of metal chelate marker groups leads as a result of the amplification of the signal via the receptor to an improved Hook sensitivity compared to test procedures with directly detectable marker groups.

The luminescent metal chelate group is preferably detected by electrochemiluminescence in which luminescent species are generated electrochemically at the surface of an electrode. The luminescence can be detected qualitatively or/and quantitatively. Examples for carrying out luminescence assays may be found in EP-A-0 580 979, WO 90/05301, WO 90/11511 and WO 92/14138. Reference is hereby made to the methods and devices for luminescence assays disclosed in these documents. The solid phase in electrochemiluminecence assays is preferably composed of microparticles, particularly preferably of magnetic microparticles which are provided with a coating which interacts with the second antigen on the solid phase. The microparticles are preferably coated with streptavidin.

The electrochemiluminescence measurement is preferably carried out in the presence of a reducing agent for the metal complex e.g. an amine. Aliphatic amines are preferred, in particular primary, secondary and tertiary alkylamines the alkyl groups of which each have one to three carbon atoms. Tripropylamine is particularly preferred. The amine can, however, also be an aromatic amine such as aniline or a heterocyclic amine.

In addition a non-ionic surface-active agent e.g. an ethoxylated phenol may optionally be present as an amplifier. Such substances are for example commercially available under the names Triton X100 or Triton N-401.

On the other hand the luminescent metal chelate group can also be detected by fluorescence in which the metal chelate is excited with a light of a suitable wavelength and the resulting fluorescence radiation is measured. Examples for carrying out fluorescence assays may be found in EP-A-0 178 450 and EP-A-0 255 534. Reference is hereby made to this disclosure.

Yet a further subject matter of the present invention is a reagent for the immunological determination of a specific antibody which contains at least one metal chelate-labelled peptide according to the invention which reacts with the antibody to be determined. If the reagent is used in a double antigen bridge test, then it preferably contains (a) the metal chelate-labelled peptide and (b) a further antigen which reacts with the antibody to be determined which is bound to a solid phase or is present in a form capable of binding to a solid phase.

The invention finally also concerns an amino acid derivative of the general formulae (Ia) or (Ib).

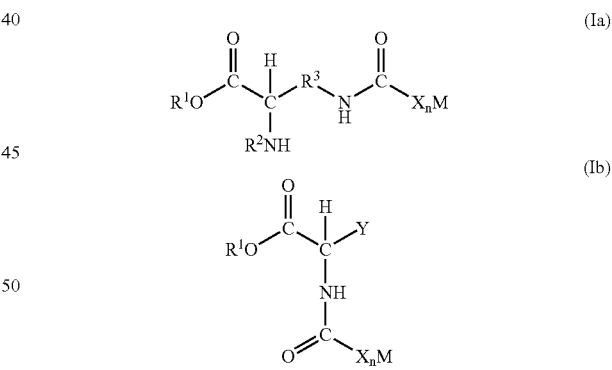

in which:
$R^1$ is hydrogen or a cationic group e.g. an alkaline metal or an ammonium ion
$R^2$ is hydrogen or an amino protecting group for the solid phase peptide synthesis
$R^3$ is a $C_1$-$C_5$ alkylene group
Y is the side chain of an arbitrary amino acid and
$MX_n$ is a luminescent metal chelate group in which the metal M is chelated by n identical or different ligands X.

In the amino acid derivative of the general formula (Ia) the metal chelate group $MX_n$ is coupled to the primary amino side group of an amino acid such as lysine or ornithine. In the amino acid derivative of the general formula (Ib) the metal chelate group is coupled to the α-amino group of an arbitrary amino acid e.g. a natural amino acid or an artificial amino acid which can optionally carry a protecting group. Amino acid derivatives of the general formula (Ia) can be introduced within or at the ends of the peptide sequence. Amino acid derivatives of the general formula (Ib) can, provided they contain no primary amino acid group in the residue Y, only be introduced at the N-terminus of the peptide sequence.

The metal chelate group $MX_n$ preferably has the structure $ML_1L_2L_3$ in which $L_1$, $L_2$, $L_3$ are the same or different and each denotes a ligand with at least 2 N-containing heterocycles e.g. bipyridiyl or phenanthrolyl and one of these ligands is optionally coupled via a spacer group to an amino group of the amino acid.

An example of a lysine-ruthenium chelate (Fmoc-Lys (BPRu)—OH) according to the invention is shown in FIG. 1.

The present invention is further described by the following examples, sequence protocols and figures.

SEQ ID NO. 1: shows the amino acid sequence of an epitope from the gp120 region of HIV I;
SEQ ID NO. 2: shows the amino acid sequence of a further epitope from the gp120 region of HIV I;
SEQ ID NO. 3: shows the amino acid sequence of a further epitope from the gp120 region of HIV I, subtype O;
SEQ ID NO. 4: shows the amino acid sequence of an epitope from the gp41 region of HIV I;
SEQ ID NO. 5: shows the amino acid sequence of a further epitope from the gp41 region of HIV I;
SEQ ID NO. 6: shows the amino acid sequence of yet a further epitope from the gp41 region of HIV I;
SEQ ID NO. 7: shows the amino acid sequence of an epitope from the gp41 region of HIV I, subtype O;
SEQ ID NO. 8: shows the amino acid sequence of a further epitope from the gp41 region of HIV I, subtype O;
SEQ ID NO. 9: shows the amino acid sequence of yet a further epitope from the gp41 region of HIV I, subtype O;
SEQ ID NO.10: shows the amino acid sequence of an epitope from the gp32 region of HIV II;
SEQ ID NO.11: shows the amino acid sequence of an epitope from the NS5 region of HCV;
SEQ ID NO.12: shows the amino acid sequence of an epitope from the Core region of HCV;
SEQ ID NO.13: shows the amino acid sequence of an epitope from the NS4 region of HCV;
SEQ ID NO.14: shows the amino acid sequence of a further epitope from the NS4 region of HCV;
SEQ ID NO.15: shows the amino acid sequence of yet a further epitope from the NS4 region of HCV;
SEQ ID NO.16: shows the amino acid sequence of a further epitope from the Core region of HCV and
SEQ ID NO.17: shows the amino acid sequence of an epitope from the NS3 region of HCV.

FIG. 1: shows a lysine derivative whose α-amino group is protected and which is coupled to ruthenium(bipyridyl)$_3$.

EXAMPLE 1

Production of Metal Chelate-labelled Peptides

The metal chelate-labelled peptides were synthesized by means of fluorenylmethyloxycarbonyl (Fmoc) solid phase peptide synthesis on a batch peptide synthesizer e.g. from Applied Biosystems A431 or A433. For this 4.0 equivalents of each of the amino acid derivatives shown in table 1 were used:

TABLE 1

| A | Fmoc-Ala-OH |
| C | Fmoc-Cys(Trt)-OH |
| D | Fmoc-Asp(OtBu)-OH |
| E | Fmoc-Glu(OtBu)-OH |
| F | Fmoc-Phe-OH |
| G | Fmoc-Gly-OH |
| H | Fmoc-His(Trt)-OH |
| I | Fmoc-Ile-OH |
| K1 | Fmoc-Lys(Boc)-OH |
| K2 | Boc-Lys(Fmoc)-OH |
| K3 | Fmoc-Lys(BPRu)-OH |
| L | Fmoc-Leu-OH |
| M | Fmoc-Met-OH |
| N | Fmoc-Asn(Trt)-OH |
| P | Fmoc-Pro-OH |
| Q | Fmoc-Gln(Trt)-OH |
| R | Fmoc-Arg(Pmc)-OH |
| S | Fmoc-Ser(tBu)-OH |
| T | Fmoc-Thr(tBu)-OH |
| U | Fmoc-βAlanine-OH |
| V | Fmoc-Val-OH |
| W | Fmoc-Trp-OH |
| Y | Fmoc-Tyr(tBu)-OH |
| Z | Fmoc-ε-aminocaproic acid-OH |
| Nle | Fmoc-ε-norleucine-OH |
| Abu | Fmoc-γ-aminobutyric acid-OH |

In variant (a)—introduction of the label after completing the solid phase synthesis—activated BPRU—COOH was coupled to the N-terminal amino acid of the peptide. The lysine derivative K1 was used for the spacer region and the lysine derivative K2 was used for the epitope region.

According to variant (b) the metal chelate groups are introduced into the peptide sequence by direct incorporation of metal chelate-coupled amino acid derivative e.g. within the sequence via a lysine residue ε-derivatized with a metal chelate active ester e.g. the lysine derivative K3 (FIG. 1) or N-terminally by using an α-derivatized amino acid residue.

The amino acids or amino acid derivatives were dissolved in N-methylpyrrolidone. The peptide was synthesized on 400-500 mg 4-(2',4'-dimethoxyphenyl-Fmoc-aminomethyl)-phenoxy resin (Tetrahedron Letters 28 (1987), 2107) with a loading of 0.4-0.7 mmol/g (JACS 95 (1973), 1328). The coupling reactions were carried out for 20 minutes iii dimethylformamide as a reaction medium with 4 equivalents dicyclohexylcarbodiimide and 4 equivalents of N-hydroxybenzotriazole relative to the Fmoc-amino acid derivative. The Fmoc group was cleaved in 20 minutes after each synthesis step using 20% piperidine in dimethylformamide.

If cysteine residues are present in the peptide sequence, an oxidation on the solid phase is carried out immediately after completion of the synthesis using iodine in hexafluoroisopropanol/dichloromethane.

The release of the peptide from the carrier and the cleavage of the acid-labile protecting groups was achieved in 40 min at room temperature with 20 ml trifluoro acetic acid, 0.5 ml ethanedithiol, 1 ml thioanisole, 1.5 g phenol and 1 ml water. The reaction solution was subsequently admixed with 300 ml cooled diisopropyl ether and kept at 0° C. for 40 min to completely precipitate the peptide. The precipitate was filtered, washed again with diisopropyl ether, dissolved in a small amount of 50% acetic acid and lyophilized. The crude material obtained was purified in ca. 120 min. by means of preparative HPLC on delta-PAK RP C18 material (column 50×300 mm, 100 Å, 15µ) using an appropriate gradient (eluant A: water, 0.1% trifluoro-acetic acid, eluant B: acetonitrile, 0.1% trifluoro-acetic acid). The identity of the eluted material was checked by means of ion spray mass spectrometry.

The metal chelate label was introduced according to variant (a) onto the free N-terminal amino group of the carrier-bound peptide by means of appropriate active ester derivatives. For this 4 equivalents BPRu—COOH per free primary amino function activated with N-hydroxy-benzotriazol/dicyclohexylcarbodiimide and dissolved in a small amount of DMSO was added dropwise and stirred at room temperature. The reaction was monitored by means of analytical HPLC. After cleavage from the carrier the product was purified by means of preparative HPLC. The identity of the eluted material was examined by means of ionspray mass spectrometry.

The peptides were also produced by a combination of variant (a) and (b) i.e. incorporation of metal chelate-coupled amino acid derivatives within the sequence, cleavage of the N-terminal Fmoc group and reaction of the free N-terminal amino group with a metal chelate active ester derivative.

In an exclusively direct incorporation of the metal chelate-coupled amino acid derivatives during the solid phase synthesis according to variant (b) it was no longer necessary to afterwards introduce metal chelate active esters.

The peptide compounds shown in Table 2 were prepared from the regions gp120, gp41 and gp32 of HIV I and HIV II.

TABLE 2

Ruthenylated linear peptides

| | |
|---|---|
| gp120 | BPRu-UZU-NNTRKSISIGPGRAFYT (SEQ ID NO: 1)<br>BPRU-UZ-NTTRSISIGPGRAFY (SEQ ID NO: 18)<br>BPRu(ethyleneglycol)-UZ-NTTRSISIGRGRAFY (SEQ ID NO: 18)<br>NNTRKSISIGPGRAFYT(SEQ ID NO: 1)-K(BPRu)<br>BPRu-UZU-IDIQEERRMRIGPGMAWYS (SEQ ID NO: 3) |
| gp41/1 | BPRu-UZU-AVERYLKDQQLLGIW (SEQ ID NO: 19)<br>BPRu-UGGG-QARILAVERYLKDQQLLGIWGASG (SEQ ID NO: 4)<br>BPRu-GGGG-QARILAVERYLKDQQLLGIWGASG (SEQ ID NO: 4)<br>BPRu-UZU-WGIRQLRARLLALETLLQN (SEQ ID NO: 9) |
| gp41/2 | BPRu-UZU-LGIWGCSGKLICTTAV (SEQ ID NO: 20)<br>BPRu-UGGG-GCSGKLICTTAVPWNASWS (SEQ ID NO: 21)<br>(GCSGKLICTTAVPWNASWS(SEQ ID NO: 21) K-(BPRu) |
| gp41/3 | BPRu-UZU-KDQQLLGIWGSSGKL (SEQ ID NO: 6) |
| gp41/4 | BPRu-UZU-ALETLLQNQQLLSLW (SEQ ID NO: 7) |
| gp32 | BPRu-UZU-NSWGCAFRQVCHTT (SEQ ID NO: 22)<br>BPRu-GGG-QAQLNSWGCAFRQVCHTTVPWPNDSLT (SEQ ID NO: 10) |

The peptides shown in the following Table 3 were synthesized from the NS5 region, the NS4 region and the Core region of HCV.

TABLE 3

Ruthenylated linear peptides

| | |
|---|---|
| Core1 | BPRu-GGGG-KNKRNTNRR (SEQ ID NO: 23) |
| Core1 + 2 | BPRu-UZU-KNKRNTNRRPQDVKFPGGGQIVGGV (SEQ ID NO: 24) |
| NS4/1 + 2 | BPRu-UZ-SQHLPYIEQG-NleNle-LAEQFKQQALGLLQT (SEQ ID NO: 25) |
| NS4/3m | BPRu-UZ-SRGNHVSPTHYVPESDAA (SEQ ID NO: 15) |
| NS5/1 | BPRu-UZ-SRRFAQALPVWARPD (SEQ ID NO: 11) |
| Core1 + 2 + 3 | BPRu-UZ-KNKRNTNRRPQDVKFPGGGQIVGGVLLPRR (SEQ ID NO: 26) |
| Core1m | BPRu-UZ-NPKPQKKNKRNTNRR (SEQ ID NO: 27) |
| Core3m | BPRu-UZ-GQIVGGVYLLPRRGPRLG (SEQ ID NO: 28) |
| Core2m | BPRu-UZ-PQDVKFPGGGQIVGGV (SEQ ID NO: 12) |
| NS4/3m-I | BPRu-UZU-SRGNHVSPTHYVPESDAA (SEQ ID NO: 15) |
| NS4/1 | BPRu-UZU-SQHLPYIEQ (SEQ ID NO: 29) |

Biotin-labelled peptides were either synthesized N-terminally by derivatization on a resin (biotin active ester) or in the sequence using a biotin-active ester ε-derivatized lysine residue (Fmoc-Lys (biotin)-OH).

EXAMPLE 2

A peptide antigen according to the invention was compared with a recombinant polypeptide antigen in a double antigen bridge test. In an example according to the invention the ruthenylated peptide antigen gp41/2 (Table 2) was tested in combination with a biotinylated peptide antigen of the same sequence. In a comparative example a ruthenylated polypeptide antigen rec. gp41 (Chang et al., Science 228 (1985), 93-96) was tested in combination with a biotinylated polypeptide antigen of the same sequence.

The results of this test showed that almost no differentiation between negative and positive samples is possible with the recombinant polypeptide antigen whereas the peptide antigen allows a very good differentiation.

The invention claimed is:

1. A method for the immunological determination of an antibody in a sample liquid, comprising
   (a) incubating a sample liquid which may contain an antibody of interest with an antigen which is directed against the antibody and comprises a peptide which has a maximum length of 50 amino acids and is coupled to at least one luminescent metal chelate label which is present on the peptide at a predetermined position on the peptide; and
   (b) determining any binding of the antibody of interest with the antigen.

2. The method as claimed in claim 1, wherein the peptide is coupled to the luminescent metal chelate at the amino terminus and/or an amino side group.

3. The method as claimed in claim 1, wherein the luminescent metal chelate is a ruthenium, rhenium, iridium or osmium chelate.

4. The method as claimed in claim 1, wherein the peptide comprises an immunologically reactive epitope region and a spacer region in which the spacer region carries the at least one luminescent metal chelate.

5. The method as claimed in claim 4, wherein the spacer region is located at the amino or/and carboxy terminus of the peptide.

6. The method as claimed in claim 4, wherein the epitope region is derived from the amino acid sequences of HIV I or HIV II.

7. The method as claimed in claim 6, wherein the epitope region is selected from the group of HIV I or HIV II amino acid sequences consisting of:

```
NNTRKSISIG PGRAFYT,              (SEQ ID NO: 1)

NTTRSISIGP GRAFYT,               (SEQ ID NO: 2)

IDIQEERRMR IGPGMAWYS,            (SEQ ID NO: 3)

QARILAVERY LKDQQLLGIW GASG,      (SEQ ID NO: 4)

LGIWGCSGKL ICTTAVPWNA SWS,       (SEQ ID NO: 5)

KDQQLLGIWG SSGKL,                (SEQ ID NO: 6)

ALETLLQNQQ LLSLW,                (SEQ ID NO: 7)

LSLWGCKGKL VCYTS,                (SEQ ID NO: 8)

WGIRQLRARL LALETLLQN and         (SEQ ID NO: 9)

QAQLNSWGCA FRQVCHTTVP WPNDSLT,   (SEQ ID NO: 10)
``` or partial sequences thereof which have a length of at least 6 amino acids.

8. The method as claimed in claim 1, wherein the method is a double-antigen bridge test.

9. A method for the immunological determination of an antibody in a sample liquid, comprising
   (a) incubating a sample liquid which may contain an antibody of interest with an antigen which is directed against the antibody and comprises a peptide which has a maximum length of 50 amino acids and is coupled to at least one luminescent metal chelate label which is present on the peptide at a predetermined position on the peptide and the peptide is prepared by at least one of the following processes:
      (1) synthesizing the peptide on a solid phase by attaching together a plurality of amino acids and/or amino acid derivatives;
         providing protecting groups on any amino side groups of the amino acids and/or amino acid derivatives to which coupling with the at least one luminescent metal chelate is to be avoided so that coupling of the at least one luminescent metal chelate in the following step may only proceed at the amino terminus of the peptide; and
         coupling the at least one luminescent metal chelate to the amino terminus, or
      (2) synthesizing the peptide on a solid phase by attaching together a plurality of amino acids and/or amino acid derivatives which are coupled to a luminescent metal chelate, wherein the amino acid derivatives are introduced at the predetermined position on the peptide; and
   (b) determining any binding of the antibody of interest with the antigen.

10. The method as claimed in claim 9, wherein the peptide is coupled to the luminescent metal chelate at the amino terminus and/or an amino side group.

11. The method as claimed in claim 9, wherein the luminescent metal chelate is a ruthenium, rhenium, iridium or osmium chelate.

12. The method as claimed in claim 9, wherein the peptide comprises an immunologically reactive epitope region and a spacer region in which the spacer region carries the at least one luminescent metal chelate.

13. The method as claimed in claim 12, wherein the spacer region is located at the amino or/and carboxy terminus of the peptide.

14. The method as claimed in claim 12, wherein the epitope region is derived from the amino acid sequences of HIV I or HIV II.

15. The method as claimed in claim 14, wherein the epitope region is selected from the group of HIV I or HIV II amino acid sequences consisting of:

| | |
|---|---|
| NNTRKSISIG PGRAFYT, | (SEQ ID NO: 1) |
| NTTRSISIGP GRAFYT, | (SEQ ID NO: 2) |
| IDIQEERRMR IGPGMAWYS, | (SEQ ID NO: 3) |
| QARILAVERY LKDQQLLGIW GASG, | (SEQ ID NO: 4) |
| LGIWGCSGKL ICTTAVPWNA SWS, | (SEQ ID NO: 5) |
| KDQQLLGIWG SSGKL, | (SEQ ID NO: 6) |
| ALETLLQNQQ LLSLW, | (SEQ ID NO: 7) |
| LSLWGCKGKL VCYTS, | (SEQ ID NO: 8) |
| WGIRQLRARL LALETLLQN and | (SEQ ID NO: 9) |
| QAQLNSWGCA FRQVCHTTVP WPNDSLT, | (SEQ ID NO: 10) | or partial sequences thereof which have a length of at least 6 amino acids.

16. The method as claimed in claim 9, wherein the method is a double-antigen bridge test.

17. A method for the immunological determination of an antibody in a sample liquid, comprising (a) incubating a sample liquid which may contain an antibody of interest with a solid phase, a first antigen which is directed against the antibody and comprises a peptide which has a maximum length of 50 amino acids and is coupled to at least one luminescent metal chelate label which is present on the peptide at a predetermined position on the peptide, and a second antigen which is directed against the antibody and either is bound to or is capable of binding to the solid phase; and (b) determining any binding of the antibody of interest with the first antigen and the second antigen by determining the label on the solid phase or/and in the liquid phase.

18. The method as claimed in claim 17, wherein the peptide is coupled to the luminescent metal chelate at the amino terminus and/or an amino side group.

19. The method as claimed in claim 17, wherein the luminescent metal chelate is a ruthenium, rhenium, iridium or osmium chelate.

20. The method as claimed in claim 17, wherein the peptide comprises an immunologically reactive epitope region and a spacer region in which the spacer region carries the at least one luminescent metal chelate.

21. The method as claimed in claim 20, wherein the spacer region is located at the amino or/and carboxy terminus of the peptide.

22. The method as claimed in claim 20, wherein the epitope region is derived from the amino acid sequences of HIV I or HIV II.

23. The method as claimed in claim 22, wherein the epitope region is selected from the group of HIV I or HIV II amino acid sequences consisting of:

| | |
|---|---|
| NNTRKSISIG PGRAFYT, | (SEQ ID NO: 1) |
| NTTRSISIGP GRAFYT, | (SEQ ID NO: 2) |
| IDIQEERRMR IGPGMAWYS, | (SEQ ID NO: 3) |
| QARILAVERY LKDQQLLGIW GASG, | (SEQ ID NO: 4) |
| LGIWGCSGKL ICTTAVPWNA SWS, | (SEQ ID NO: 5) |
| KDQQLLGIWG SSGKL, | (SEQ ID NO: 6) |
| ALETLLQNQQ LLSLW, | (SEQ ID NO: 7) |
| LSLWGCKGKL VCYTS, | (SEQ ID NO: 8) |
| WGIRQLRARL LALETLLQN and | (SEQ ID NO: 9) |
| QAQLNSWGCA FRQVCHTTVP WPNDSLT, | (SEQ ID NO: 10) | or partial sequences thereof which have a length of at least 6 amino acids.

24. The method of claim 17, wherein the second antigen is labeled with biotin, and the solid phase is coated with streptavidin or avidin.

25. The method of claim 24, wherein the second antigen comprises a peptide labeled with biotin.

26. The method of claim 17, wherein the solid phase comprises magnetic particles.

27. A method for the immunological determination of an antibody in a sample liquid, comprising (a) incubating a sample liquid which may contain an antibody of interest with a solid phase, a first antigen which is directed against the antibody and comprises a peptide which has a maximum length of 50 amino acids and is coupled to at least one luminescent metal chelate label which is present on the peptide at a predetermined position on the peptide and the peptide is prepared by at least one of the following processes:

(1) synthesizing the peptide on a solid phase by attaching together a plurality of amino acids and/or amino acid derivatives;

providing protecting groups on any amino side groups of the amino acids and/or amino acid derivatives to which coupling with the at least one luminescent metal chelate is to be avoided so that coupling of the at least one luminescent metal chelate in the following step may only proceed at the amino terminus of the peptide; and coupling the at least one luminescent metal chelate to the amino terminus, or (2) synthesizing the peptide on a solid phase by attaching together a plurality of amino acids and/or amino acid derivatives which are coupled to a luminescent metal chelate, wherein the amino acid derivatives are introduced at the predetermined position on the peptide, and a second antigen which is directed against the antibody and either is bound to or is capable of binding to the solid phase; and (b) determining any binding of the antibody of interest with the first antigen and the second antigen by determining the label on the solid phase or/and in the liquid phase.

28. The method as claimed in claim 27, wherein the peptide is coupled to the luminescent metal chelate at the amino terminus and/or an amino side group.

29. The method as claimed in claim 27, wherein the luminescent metal chelate is a ruthenium, rhenium, iridium or osmium chelate.

30. The method as claimed in claim 27, wherein the peptide comprises an immunologically reactive epitope region and a spacer region in which the spacer region carries the at least one luminescent metal chelate.

31. The method as claimed in claim 30, wherein the spacer region is located at the amino or/and carboxy terminus of the peptide.

32. The method as claimed in claim 30, wherein the epitope region is derived from the amino acid sequences of HIV I or HIV II.

33. The method as claimed in claim 32, wherein the epitope region is selected from the group of HIV I or HIV II amino acid sequences consisting of:

```
NNTRKSISIG PGRAFYT,            (SEQ ID NO: 1)
NTTRSISIGP GRAFYT,             (SEQ ID NO: 2)
IDIQEERRMR IGPGMAWYS,          (SEQ ID NO: 3)
QARILAVERY LKDQQLLGIW GASG,    (SEQ ID NO: 4)
LGIWGCSGKL ICTTAVPWNA SWS,     (SEQ ID NO: 5)
KDQQLLGIWG SSGKL,              (SEQ ID NO: 6)
ALETLLQNQQ LLSLW,              (SEQ ID NO: 7)
LSLWGCKGKL VCYTS,              (SEQ ID NO: 8)
WGIRQLRARL LALETLLQN and       (SEQ ID NO: 9)
QAQLNSWGCA FRQVCHTTVP WPNDSLT, (SEQ ID NO: 10)
``` or partial sequences thereof which have a length of at least 6 amino acids.

34. The method of claim 27, wherein the second antigen is labeled with biotin, and the solid phase is coated with streptavidin or avidin.

35. The method of claim 34, wherein the second antigen comprises a peptide labeled with biotin.

36. The method of claim 27, wherein the solid phase comprises magnetic particles.

* * * * *